(12) United States Patent
Landey et al.

(10) Patent No.: US 10,285,574 B2
(45) Date of Patent: May 14, 2019

(54) SUPERELASTIC MEDICAL INSTRUMENT

(71) Applicant: Auris Health, Inc., Redwood City, CA (US)

(72) Inventors: Casey Teal Landey, San Francisco, CA (US); Ryan Jeffrey Connolly, San Carlos, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 15/944,566

(22) Filed: Apr. 3, 2018

(65) Prior Publication Data

US 2018/0289243 A1    Oct. 11, 2018

Related U.S. Application Data

(60) Provisional application No. 62/483,131, filed on Apr. 7, 2017.

(51) Int. Cl.
| | | |
|---|---|---|
| A61B 1/005 | (2006.01) | |
| A61L 31/02 | (2006.01) | |
| A61B 10/04 | (2006.01) | |
| A61B 1/018 | (2006.01) | |
| A61B 1/267 | (2006.01) | |
| A61B 17/34 | (2006.01) | |
| A61B 34/30 | (2016.01) | |
| A61B 10/02 | (2006.01) | |
| A61L 31/14 | (2006.01) | |
| A61B 17/00 | (2006.01) | |
| A61B 1/313 | (2006.01) | |
| A61B 90/00 | (2016.01) | |

(52) U.S. Cl.
CPC .......... *A61B 1/0058* (2013.01); *A61B 1/0051* (2013.01); *A61B 1/018* (2013.01); *A61B 1/2676* (2013.01); *A61B 10/04* (2013.01); *A61B 17/3403* (2013.01); *A61B 34/30* (2016.02); *A61L 31/022* (2013.01); *A61B 1/3132* (2013.01); *A61B 2010/0216* (2013.01); *A61B 2010/045* (2013.01); *A61B 2017/00867* (2013.01); *A61B 2090/3966* (2016.02); *A61L 31/14* (2013.01)

(58) Field of Classification Search
CPC ...... A61B 1/0058; A61B 10/04; A61L 31/022
USPC ........................................................ 600/567
See application file for complete search history.

(56) References Cited

U.S. PATENT DOCUMENTS

| | | | |
|---|---|---|---|
| 4,040,413 A | 8/1977 | Ohshiro | |
| 4,198,960 A | 4/1980 | Utsugi | |
| 4,470,407 A | 9/1984 | Hussein | |
| 4,685,458 A | 8/1987 | Leckrone | |
| 4,747,405 A | 5/1988 | Leckrone | |

(Continued)

FOREIGN PATENT DOCUMENTS

| | | |
|---|---|---|
| WO | WO 11/161218 | 12/2011 |
| WO | WO 13/107468 | 7/2013 |
| WO | WO 13/130895 | 9/2013 |

*Primary Examiner* — Daniel L Cerioni
(74) *Attorney, Agent, or Firm* — Knobbe, Martens, Olson & Bear, LLP

(57) ABSTRACT

Certain aspects relate to a superelastic medical instrument that of bending elastically through the tortuous pathways of an endoscope, returning to a straight shape upon deployment from the endoscope, and deploying straight along the axis of the end of the bronchoscope (within a tolerated margin) to distances of 2 cm or more.

29 Claims, 8 Drawing Sheets

(56) References Cited

U.S. PATENT DOCUMENTS

| | | | |
|---|---|---|---|
| 4,898,574 A | 2/1990 | Uchiyama et al. | |
| 4,983,165 A | 1/1991 | Loiterman | |
| 5,029,574 A | 7/1991 | Shimarnura et al. | |
| 5,085,659 A | 2/1992 | Rydell | |
| 5,308,323 A | 5/1994 | Sogawa et al. | |
| 5,325,848 A | 7/1994 | Adams et al. | |
| 5,344,395 A | 9/1994 | Whalen et al. | |
| 5,353,783 A | 10/1994 | Nakao et al. | |
| 5,370,609 A | 12/1994 | Drasler et al. | |
| 5,372,124 A | 12/1994 | Takayama et al. | |
| 5,411,016 A | 5/1995 | Kume | |
| 5,431,649 A | 7/1995 | Mulier et al. | |
| 5,441,485 A | 8/1995 | Peters | |
| 5,450,843 A | 9/1995 | Moll et al. | |
| 5,472,426 A | 12/1995 | Bonati et al. | |
| 5,501,667 A | 3/1996 | Verduin, Jr. | |
| 5,520,684 A | 5/1996 | Imran | |
| 5,562,678 A | 10/1996 | Booker | |
| 5,572,999 A | 11/1996 | Funda et al. | |
| 5,613,973 A | 3/1997 | Jackson et al. | |
| 5,645,083 A | 7/1997 | Essig et al. | |
| 5,653,374 A | 8/1997 | Young et al. | |
| 5,658,311 A | 8/1997 | Baden | |
| 5,695,500 A | 12/1997 | Taylor et al. | |
| 5,716,325 A | 2/1998 | Bonutti | |
| 5,788,667 A | 8/1998 | Stolier | |
| 5,810,770 A | 9/1998 | Chin et al. | |
| 5,924,175 A | 7/1999 | Lippitt | |
| 5,989,230 A | 11/1999 | Frassica | |
| 6,071,281 A | 6/2000 | Burnside et al. | |
| 6,093,157 A * | 7/2000 | Chandrasekaran | A61B 17/320758 600/585 |
| 6,120,476 A | 9/2000 | Fung et al. | |
| 6,120,498 A | 9/2000 | Jani et al. | |
| 6,156,030 A | 12/2000 | Neev | |
| 6,174,318 B1 | 1/2001 | Bates et al. | |
| 6,405,078 B1 | 6/2002 | Moaddeb et al. | |
| 6,440,061 B1 | 8/2002 | Wenner et al. | |
| 6,508,823 B1 | 1/2003 | Gonon | |
| 6,522,906 B1 | 2/2003 | Salisbury et al. | |
| 6,577,891 B1 | 6/2003 | Jaross et al. | |
| 6,676,668 B2 | 1/2004 | Mercereau et al. | |
| 6,706,050 B1 | 3/2004 | Giannadakis | |
| 7,282,055 B2 | 10/2007 | Tsuruta | |
| 7,963,911 B2 | 6/2011 | Turliuc | |
| 8,038,598 B2 | 10/2011 | Khachi | |
| 8,092,397 B2 | 1/2012 | Wallace et al. | |
| 8,187,173 B2 | 5/2012 | Miyoshi | |
| 8,257,303 B2 | 9/2012 | Moll et al. | |
| 8,523,762 B2 | 9/2013 | Miyamoto et al. | |
| 8,956,280 B2 | 2/2015 | Eversull et al. | |
| 9,460,536 B2 | 10/2016 | Hasegawa et al. | |
| 9,504,604 B2 | 11/2016 | Alvarez | |
| 9,561,083 B2 | 2/2017 | Yu et al. | |
| 9,592,042 B2 | 3/2017 | Titus | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,844,412 B2 | 12/2017 | Bogusky et al. | |
| 9,867,635 B2 | 1/2018 | Alvarez et al. | |
| 9,931,025 B1 | 4/2018 | Graetzel et al. | |
| 2002/0019644 A1 | 2/2002 | Hastings | |
| 2003/0040681 A1* | 2/2003 | Ng | A61B 10/02 600/562 |
| 2003/0109889 A1 | 6/2003 | Mercereau | |
| 2004/0143253 A1 | 7/2004 | Vanney | |
| 2004/0158261 A1 | 8/2004 | Vu | |
| 2004/0186349 A1 | 9/2004 | Ewers | |
| 2004/0210116 A1 | 10/2004 | Nakao | |
| 2005/0159645 A1 | 7/2005 | Bertolero | |
| 2005/0261705 A1 | 11/2005 | Gist | |
| 2006/0015133 A1 | 1/2006 | Grayzel | |
| 2006/0058813 A1 | 3/2006 | Teague | |
| 2006/0116693 A1 | 6/2006 | Weisenburgh | |
| 2006/0135963 A1 | 6/2006 | Kick | |
| 2006/0156875 A1 | 7/2006 | McRury et al. | |
| 2006/0189891 A1* | 8/2006 | Waxman | A61B 10/0233 600/564 |
| 2007/0027534 A1 | 2/2007 | Bergheim | |
| 2007/0032906 A1 | 2/2007 | Sutherland et al. | |
| 2007/0106304 A1 | 5/2007 | Hammack | |
| 2007/0135603 A1 | 6/2007 | Belson | |
| 2007/0213668 A1 | 9/2007 | Spitz | |
| 2007/0250111 A1 | 10/2007 | Lu | |
| 2007/0299427 A1 | 12/2007 | Yeung et al. | |
| 2008/0033467 A1 | 2/2008 | Miyamoto et al. | |
| 2008/0125698 A1 | 5/2008 | Greg et al. | |
| 2008/0187101 A1 | 8/2008 | Gertner | |
| 2008/0228104 A1 | 9/2008 | Uber et al. | |
| 2009/0012507 A1 | 1/2009 | Culbertson et al. | |
| 2009/0036900 A1 | 2/2009 | Moll | |
| 2009/0082634 A1 | 3/2009 | Kathrani et al. | |
| 2009/0105723 A1 | 4/2009 | Dillinger | |
| 2009/0161827 A1 | 6/2009 | Gertner | |
| 2009/0248041 A1 | 10/2009 | Williams et al. | |
| 2009/0248043 A1 | 10/2009 | Tierney et al. | |
| 2009/0264878 A1 | 10/2009 | Carmel et al. | |
| 2010/0204605 A1* | 8/2010 | Blakley | A61B 5/01 600/549 |
| 2010/0217235 A1* | 8/2010 | Thorstenson | A61M 25/0012 604/527 |
| 2011/0015483 A1 | 1/2011 | Barbagli | |
| 2011/0071541 A1 | 3/2011 | Prisco et al. | |
| 2011/0071543 A1 | 3/2011 | Prisco et al. | |
| 2011/0125165 A1 | 5/2011 | Simaan et al. | |
| 2011/0224660 A1 | 9/2011 | Neuberger et al. | |
| 2011/0257641 A1 | 10/2011 | Hastings et al. | |
| 2011/0313343 A1 | 12/2011 | Milutinovic et al. | |
| 2012/0138586 A1 | 6/2012 | Webster et al. | |
| 2012/0232342 A1 | 9/2012 | Reydel | |
| 2012/0253332 A1 | 10/2012 | Moll | |
| 2012/0259320 A1 | 10/2012 | Loesel et al. | |
| 2012/0296318 A1 | 11/2012 | Wellhofer et al. | |
| 2013/0006144 A1* | 1/2013 | Clancy | A61B 10/04 600/567 |
| 2013/0066136 A1 | 3/2013 | Palese et al. | |
| 2013/0085442 A1 | 4/2013 | Shtul et al. | |
| 2013/0085486 A1 | 4/2013 | Boutoussov et al. | |
| 2013/0096574 A1 | 4/2013 | Kang et al. | |
| 2013/0110042 A1 | 5/2013 | Humphreys | |
| 2013/0116716 A1 | 5/2013 | Bahls et al. | |
| 2013/0190796 A1 | 7/2013 | Tilson et al. | |
| 2013/0253267 A1 | 9/2013 | Collins | |
| 2013/0303876 A1 | 11/2013 | Gelfand et al. | |
| 2013/0310619 A1 | 11/2013 | Neuberger et al. | |
| 2014/0039681 A1 | 2/2014 | Bowling | |
| 2014/0051985 A1 | 2/2014 | Fan | |
| 2014/0058404 A1 | 2/2014 | Hammack | |
| 2014/0142591 A1 | 5/2014 | Alvarez et al. | |
| 2014/0163318 A1 | 6/2014 | Swanstrom | |
| 2014/0194859 A1 | 7/2014 | Ianchulev | |
| 2014/0275956 A1 | 9/2014 | Fan | |
| 2014/0309649 A1 | 10/2014 | Alvarez et al. | |
| 2014/0309655 A1 | 10/2014 | Gal et al. | |
| 2014/0316203 A1 | 10/2014 | Carroux et al. | |
| 2014/0357984 A1 | 12/2014 | Wallace et al. | |
| 2014/0364870 A1 | 12/2014 | Alvarez et al. | |
| 2014/0379000 A1 | 12/2014 | Romo et al. | |
| 2015/0051592 A1 | 2/2015 | Kintz | |
| 2015/0101442 A1 | 4/2015 | Romo | |
| 2015/0119638 A1 | 4/2015 | Yu et al. | |
| 2015/0164594 A1 | 6/2015 | Romo et al. | |
| 2015/0164596 A1 | 6/2015 | Romo | |
| 2015/0202085 A1 | 7/2015 | Lemonis | |
| 2015/0314110 A1 | 11/2015 | Park | |
| 2015/0335480 A1 | 11/2015 | Alvarez et al. | |

(56) References Cited

U.S. PATENT DOCUMENTS

| | | |
|---|---|---|
| 2016/0001038 A1 | 1/2016 | Romo et al. |
| 2016/0022289 A1 | 1/2016 | Wan |
| 2016/0030073 A1 | 2/2016 | Lsakov |
| 2016/0158490 A1* | 6/2016 | Leeflang .......... A61M 25/0012 604/527 |
| 2016/0183841 A1 | 6/2016 | Duindam et al. |
| 2016/0235495 A1 | 8/2016 | Wallace et al. |
| 2016/0249932 A1 | 9/2016 | Rogers et al. |
| 2016/0270865 A1 | 9/2016 | Landey et al. |
| 2016/0279394 A1 | 9/2016 | Moll et al. |
| 2016/0287279 A1 | 10/2016 | Bovay et al. |
| 2016/0296294 A1 | 10/2016 | Moll et al. |
| 2016/0331358 A1* | 11/2016 | Gordon ................. A61B 10/04 |
| 2016/0367324 A1 | 12/2016 | Sato et al. |
| 2016/0374541 A1 | 12/2016 | Agrawal et al. |
| 2017/0007337 A1 | 1/2017 | Dan |
| 2017/0065227 A1 | 3/2017 | Marrs |
| 2017/0065364 A1 | 3/2017 | Schuh et al. |
| 2017/0065365 A1 | 3/2017 | Schuh |
| 2017/0095234 A1* | 4/2017 | Prisco ..................... A61B 1/00 |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055583 A1 | 3/2018 | Schuh et al. |

* cited by examiner

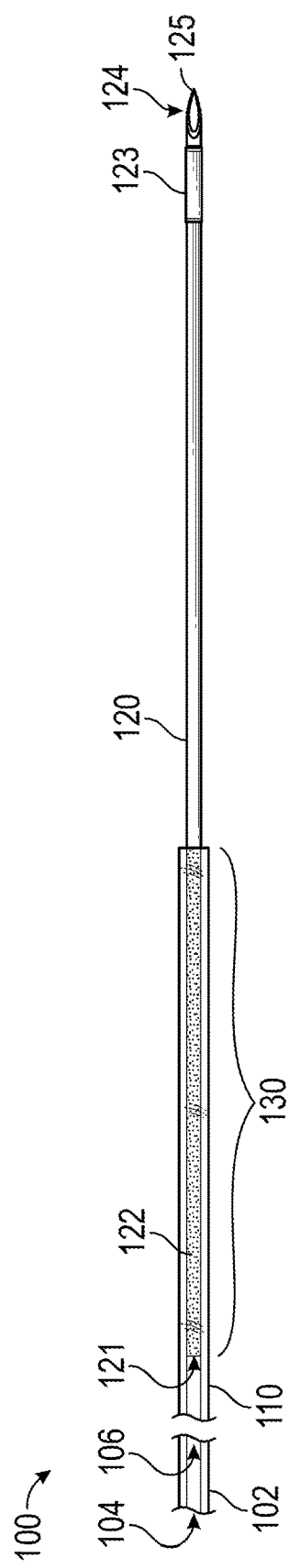
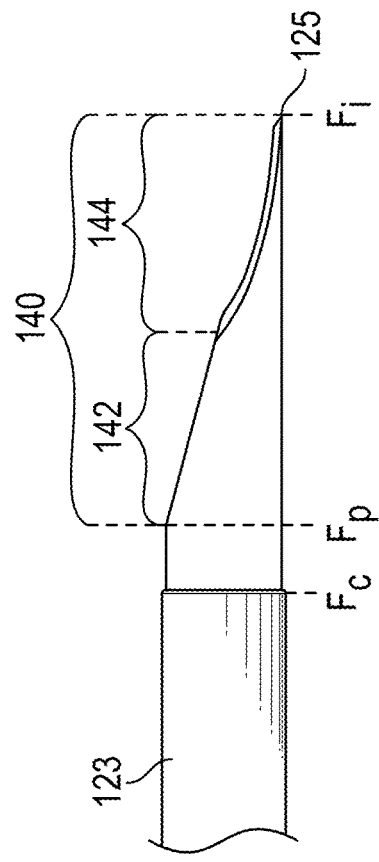
FIG. 1A
FIG. 1B

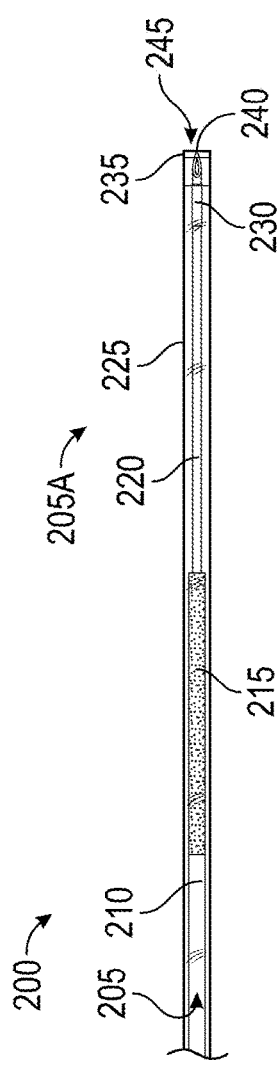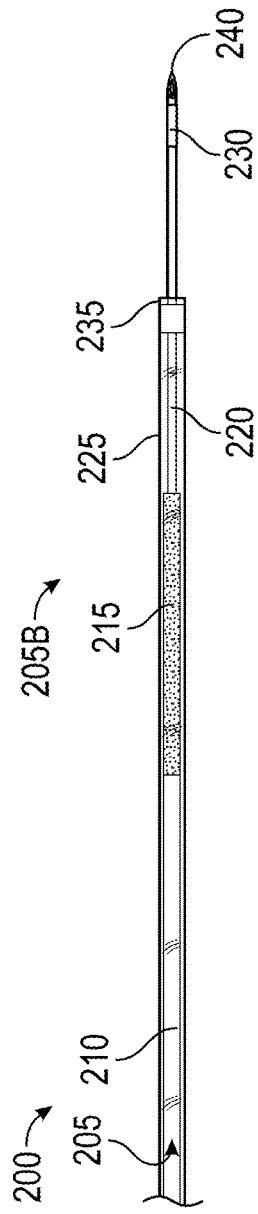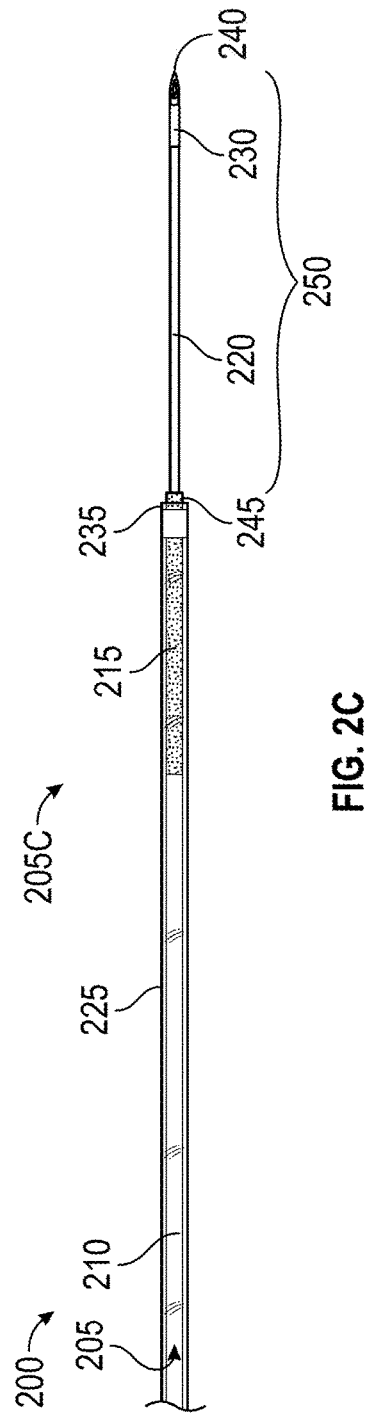

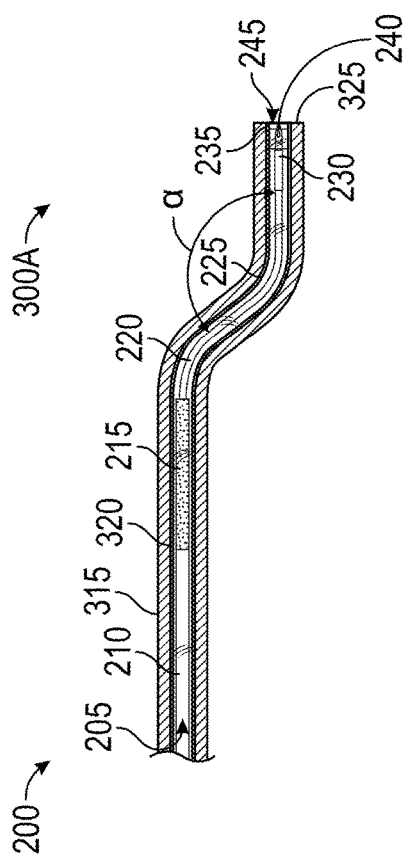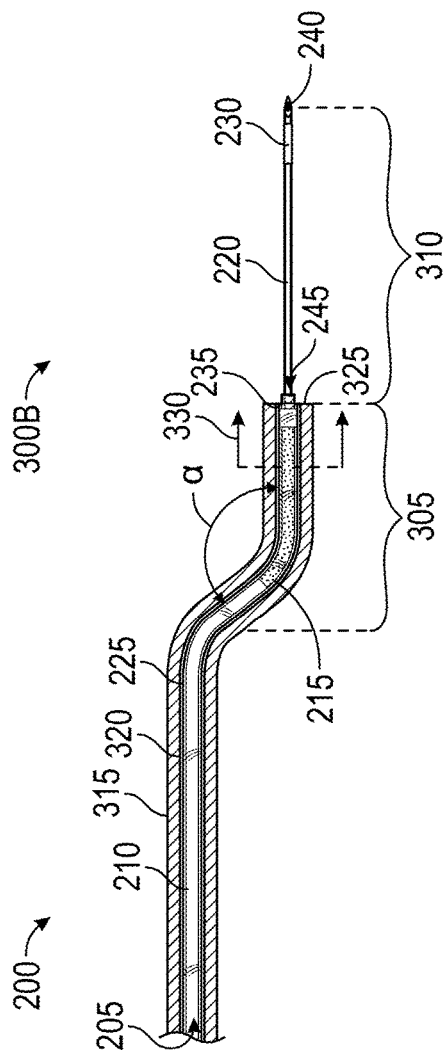

SUPERELASTIC MEDICAL INSTRUMENT

CROSS-REFERENCE TO RELATED APPLICATION(S)

The present application claims the benefit under 35 U.S.C. § 119(e) of U.S. Provisional Patent Application No. 62/483,131, filed on Apr. 7, 2017, entitled "SUPERELASTIC MEDICAL INSTRUMENT," the contents of which are hereby incorporated by reference herein in their entirety.

TECHNICAL FIELD

The present disclosure relates generally to medical devices, and more particularly to a superelastic medical instruments.

BACKGROUND

Endoscopy (e.g., bronchoscopy) may involve accessing and visualizing the inside of a patient's luminal network for diagnostic and/or therapeutic purposes. During a procedure a flexible tubular tool, known as an endoscope, may be inserted into the patient's body and a tool can be passed down through the endoscope to a tissue site identified for subsequent diagnosis and/or treatment. The endoscope can have an interior lumen (e.g., "working channel") providing a pathway to the tissue site, and catheters and/or various medical tools can be inserted through the working channel to the tissue site.

SUMMARY

The systems, methods and devices of this disclosure each have several innovative aspects, no single one of which is solely responsible for the desirable attributes disclosed herein.

Accordingly, one aspect relates to a biopsy needle assembly, comprising a needle formed from a superelastic alloy, the needle including a body portion extending from a distal end of the needle to a proximal end of the needle, and an inner surface of the needle forming a lumen extending through at least a portion of the body portion to an opening in the distal end, wherein the lumen and the opening are configured to acquire a tissue biopsy; an elongate shaft attached at the proximal end of the needle; and a tubular jacket including an interior channel, wherein in a first configuration, the distal end of the needle is positioned within the interior channel, and in a second configuration, in response to distal movement of the elongate shaft through the interior channel, the distal end of the needle is extended beyond a distal end of the tubular jacket.

In some implementations, the superelastic alloy comprises Nitinol. In some implementations, the needle has a wall thickness of approximately 0.0015 inches thick.

Some implementations further comprise a sharpened tip at the distal end of the needle. Some implementations further comprise a radiopaque material positioned around the needle near the sharpened tip. In some implementations, the radiopaque material comprises gold. In some implementations, the radiopaque material has a thickness of at least 200 microinches.

In some implementations, the elongate shaft comprises a polymer tube reflowed around an overlap region located at the proximal end of the needle. In some implementations, the polymer tube comprises a conical section at its distal end prior to or after being reflowed around the overlap region. In some implementations, the polymer tube comprises a flexible thermoplastic. In some implementations, the needle has a length of approximately 5 centimeters from the distal end to the proximal end, and wherein the overlap region has a length of approximately 2 centimeters. In some implementations, the needle has a length of approximately 4 centimeters from the distal end to the proximal end, and wherein the overlap region has a length of approximately 1 centimeters. In some implementations, the needle has a length between 1 centimeter and 6 centimeters. In some implementations, the overlap region has a length of 0.5 cm to 3 cm. In some implementations, a channel formed by an interior surface of the polymer tube is in fluid communication with the lumen to provide pressure through the opening.

In some implementations, the elongate shaft comprises a polymer tube reflowed around an overlap region located at the proximal end of the needle, and the assembly further comprises a plurality of surface features formed on the needle at the overlap region, wherein the polymer tube is reflowed around the surface features. In some implementations, the plurality of surface features comprise a grit blasted exterior surface of the needle. In some implementations, plurality of surface features comprise laser cut holes each extending through a wall of the needle. In some implementations, the overlap region is located at a distal end of the tube. In some implementations, the proximal end of the needle includes a first spiral channel or cut, and the distal end of the tube includes a second spiral channel or cut structured to mechanically mate with the first spiral channel or cut. In some implementations, proximal end of the needle and the distal end of the tube are secured at the overlap region by a flexible adhesive. In some implementations, proximal end of the needle and the distal end of the tube are secured at the overlap region by screws.

In some implementations, the superelastic alloy, in its austenite phase, is in an original shape in which the body portion is straight. In some implementations, the superelastic alloy, in its martensite phase, deforms reversibly up to 10% from the original shape.

Another aspect relates to a method of obtaining a tissue biopsy, the method comprising positioning a distal end of a working channel of an endoscope adjacent to a desired biopsy site; advancing a tubular jacket through the working channel, the jacket including a biopsy needle assembly positioned within the jacket, the biopsy needle assembly comprising a needle formed from a superelastic alloy, the needle including a body portion extending from a distal end of the needle to a proximal end of the needle, and an inner surface of the needle forming a lumen extending through at least a portion of the body portion to an opening in the distal end, wherein the lumen and the opening are configured to acquire a tissue biopsy; and an elongate shaft attached at the proximal end of the needle; actuating a first linear motion of a proximal end the elongate shaft to drive extension of at least a portion of the needle out of the jacket into the biopsy site; acquiring a tissue sample from the biopsy site through the opening of the needle; and actuating a second linear motion of the proximal end the elongate shaft to drive retraction of the needle out of the biopsy site.

Some implementations further comprise applying a pressure within the lumen to acquire the tissue biopsy. In some implementations, the jacket has a handle coupled to a proximal end of the jacket configured to actuate the first and second linear motions of the proximal end of the elongate shaft along a longitudinal axis of the handle, the method further comprising actuating the handle to control the extension and the retraction of the needle. Some implementations further comprise robotically controlling actuation of the handle.

In some implementations, the elongate shaft comprises a polymer tube secured at an overlap region at the proximal end of the needle, and the method further comprises positioning a distal end of the jacket a predetermined distance from the tissue site, the predetermined distance being less than a length of the needle extending distally beyond the overlap region; and wherein actuating the first linear motion comprises performing a first drive of the needle to extend the needle out of the jacket; determining that the distal end of the needle is positioned out of the jacket; and performing a second drive of the needle to extend the needle into the biopsy site. Some implementations further comprise determining, after the first drive and before the second drive, that the overlap region is still positioned at least partly within the jacket. Some implementations further comprise determining, after the first drive and before the second drive, that the overlap region is still positioned at least partly within the working channel of the endoscope. In some implementations, performing the second drive comprises alternating extending the needle into the biopsy site and retracting the needle from the biopsy site a plurality of times.

Some implementations further comprise viewing the biopsy site using fluoroscopy; and determining that the distal end of the needle is positioned at the biopsy site by viewing, via the fluoroscopy, a radiopaque material positioned around the needle near the distal end.

In some implementations, advancing the tubular jacket through the working channel comprises advancing the needle through a curved portion of the working channel, and advancing the needle through the curved portion reversibly deforms the needle up to 10% from an original shape of the needle in which the body portion is straight. In some implementations, reversibly deforming the needle comprises causing the superelastic alloy to transition from an austenite phase in which the needle is in the original shape to a martensite state. In some implementations, driving extension of at least the portion of the needle out of the jacket into the biopsy site includes causing at least the portion of the needle to automatically transition back to the austenite phase and revert to the original shape.

Another aspect relates to a robotic needle biopsy system, comprising a needle formed from a superelastic material, the needle including an inner surface forming a lumen extending from an opening in a proximal end of the needle through a body portion of the needle to an opening in a distal end of the needle, wherein the lumen and the opening in the distal end are configured to acquire a tissue biopsy; an elongate shaft secured at the proximal end of the needle; a tubular jacket including an interior channel positioned around at least a portion of the needle and the elongate shaft; and a control system configured to move the elongate shaft to drive the needle between a first configuration and a second configuration, wherein in the first configuration the distal end of the needle is positioned within the interior channel of the tubular jacket, and wherein in the second configuration the distal end of the needle is extended beyond a distal end of the tubular jacket.

In some implementations, the needle further comprises a sharpened tip at the distal end of the needle. In some implementations, the needle further comprises a radiopaque material positioned around the body portion of the needle near the sharpened tip. In some implementations, the radiopaque material comprises a gold pattern. In some implementations, the radiopaque material has a thickness ranging from approximately 200 to approximately 1000 microinches.

In some implementations, the elongate shaft comprises a polymer tube secured around an overlap region located at the proximal end of the needle. In some implementations, the polymer tube comprises a flexible thermoplastic reflowed around the overlap region. In some implementations, needle has a length of approximately 5 cm from the distal end to the proximal end, and wherein the overlap region has a length of approximately 2 cm. In some implementations, robotic system is configured to advance the distal end of the needle up to 3 cm beyond the distal end of the tubular jacket in the second configuration. In some implementations, needle has a length of approximately 4 cm from the distal end to the proximal end, and wherein the overlap region has a length of approximately 1 cm. In some implementations, robotic system is configured to advance the distal end of the needle up to 2 cm beyond the distal end of the tubular jacket in the second configuration. In some implementations, needle has a length between 1 centimeter and 6 centimeters. In some implementations, overlap region has a length of 0.5 cm to 3 cm. In some implementations, the robotic needle biopsy system further comprises a source of pressure coupled to a proximal end of the polymer tube, and the robotic system is configured to provide the pressure through the opening at the distal end of the needle via a channel formed by an interior surface of the polymer tube in fluid communication with the lumen of the needle.

In some implementations, the elongate shaft comprises a polymer tube secured around an overlap region located at the proximal end of the needle, and the proximal end of the needle includes a first spiral channel or cut, and a distal end of the tube includes a second spiral channel or cut structured to mechanically mate with the first spiral channel or cut. In some implementations, the proximal end of the needle and a distal end of the tube are secured at the overlap region by a flexible adhesive instead of or in addition to mechanically mating. In some implementations, the proximal end of the needle and a distal end of the tube are secured at the overlap region by screws in addition to mechanically mating via the spiral channels and/or being secured by adhesive.

In some implementations, the elongate shaft comprises a polymer tube secured around an overlap region located at the proximal end of the needle, and the needle further comprising a plurality of surface features formed at the overlap region, wherein the polymer tube is reflowed around the surface features. In some implementations, the plurality of surface features comprise a grit blasted exterior surface of the needle. In some implementations, the plurality of surface features comprise laser cut holes each extending through a wall of the needle.

In some implementations, the needle has a wall thickness of approximately 0.0015 inches thick. In some implementations, the control system comprises a computer-readable memory storing instructions and one or more processors configured by the instructions to drive the needle between the first configuration and the second configuration.

Some implementations further comprise an endoscope including a working channel, wherein the jacket is positioned at least partly within the working channel. In some implementations, the endoscope comprises at least one actuation cable, wherein the control system is further configured to detect a change in tension on the at least one actuation cable; identify a deflection condition at a distal tip of the endoscope due to passage of the needle through a curved portion of the working channel near the distal tip of the endoscope; and adjust the tension on the at least one actuation cable to compensate for the deflection condition.

Another aspect relates to a medical instrument assembly, comprising a medical instrument extending from a proximal end to a distal end and including a superelastic shaft formed from a superelastic alloy, the superelastic shaft extending from the distal end of the medical instrument at least partway to the proximal end; an elongate shaft attached at the proximal end of the medical instrument; and a tubular jacket including an interior channel, wherein in a first configuration, the distal end of the medical instrument is positioned within the interior channel, and in a second configuration, in response to distal movement of the elongate shaft through the interior channel, the distal end of the medical instrument is medical instrument beyond a distal end of the tubular jacket.

In some implementations, the superelastic material comprises Nitinol. In some implementations, the medical instrument comprises a brush at the distal end.

Some implementations further comprise a radiopaque material positioned around the superelastic shaft near the distal end of the medical instrument. In some implementations, the radiopaque material comprises a gold band. In some implementations, the radiopaque material has a thickness of at least 200 microinches.

In some implementations, the elongate shaft comprises a polymer tube reflowed around an overlap region located at the proximal end of the superelastic shaft. In some implementations, the polymer tube comprises a conical section at its distal end prior to or after being reflowed around the overlap region. In some implementations, the polymer tube comprises a flexible thermoplastic. In some implementations, the superelastic shaft has a length of approximately 5 centimeters from the distal end to the proximal end, and wherein the overlap region has a length of approximately 2 centimeters. In some implementations, the superelastic shaft has a length of approximately 4 centimeters from the distal end to the proximal end, and wherein the overlap region has a length of approximately 1 centimeters. In some implementations, the superelastic shaft has a length between 1 centimeter and 6 centimeters. In some implementations, the overlap region has a length of 0.5 cm to 3 cm.

In some implementations, the elongate shaft comprises a polymer tube reflowed around an overlap region located at the proximal end of the superelastic shaft, the In some implementations, the elongate shaft comprises a polymer tube reflowed around an overlap region located at the proximal end of the superelastic shaft further comprising a plurality of surface features formed on the superelastic shaft at the overlap region, wherein the polymer tube is reflowed around the surface features. In some implementations, the plurality of surface features comprise a grit blasted exterior surface of the superelastic shaft. In some implementations, the plurality of surface features comprise laser cut holes each extending through a wall of the superelastic shaft.

In some implementations, the superelastic shaft is tubular. In some implementations, the elongate shaft comprises a polymer tube secured around an overlap region located at the proximal end of the superelastic shaft and a distal end of the tube. In some implementations, the proximal end of the superelastic shaft includes a first spiral channel or cut, and the distal end of the tube includes a second spiral channel or cut structured to mechanically mate with the first spiral channel or cut. In some implementations, the proximal end of the superelastic shaft and the distal end of the tube are secured at the overlap region by a flexible adhesive. In some implementations, the proximal end of the superelastic shaft and the distal end of the tube are secured at the overlap region by screws.

Another aspect relates to a medical device, comprising a medical instrument extending from a proximal end to a distal end and including a superelastic shaft formed from a superelastic alloy, the superelastic shaft extending from the distal end of the medical instrument at least partway to the proximal end; an elongate shaft attached at the proximal end of the medical instrument; a tubular jacket including an interior channel, wherein in a first configuration, the distal end of the medical instrument is positioned within the interior channel, and in a second configuration, in response to distal movement of the elongate shaft through the interior channel, the distal end of the medical instrument is medical instrument beyond a distal end of the tubular jacket; and a handle including a distal end coupled to a proximal end of the jacket, an internal drive member coupled to a proximal end of the elongate shaft, a movable grip, and at least one motion transmitting interface configured to actuate the distal movement of the elongate shaft through the interior channel in response to user movement of the movable grip.

In some implementations, the superelastic material comprises Nitinol. In some implementations, the medical instrument comprises a brush at the distal end. In some implementations, the medical instrument comprises a needle including an inner surface forming a lumen extending from an opening in a proximal end of the needle through a body portion of the needle to an opening in a distal end of the needle, wherein the lumen and the opening in the distal end are configured to acquire a tissue biopsy.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIGS. 1A and 1B illustrate an embodiment of a superelastic needle as described herein.

FIGS. 2A-2C illustrate various configurations of a needle assembly as described herein.

FIGS. 3A and 3B illustrate the needle assembly of FIGS. 2A-2C exhibiting superelastic properties in retracted and extended configurations.

DETAILED DESCRIPTION

Introduction

Figure 3C:
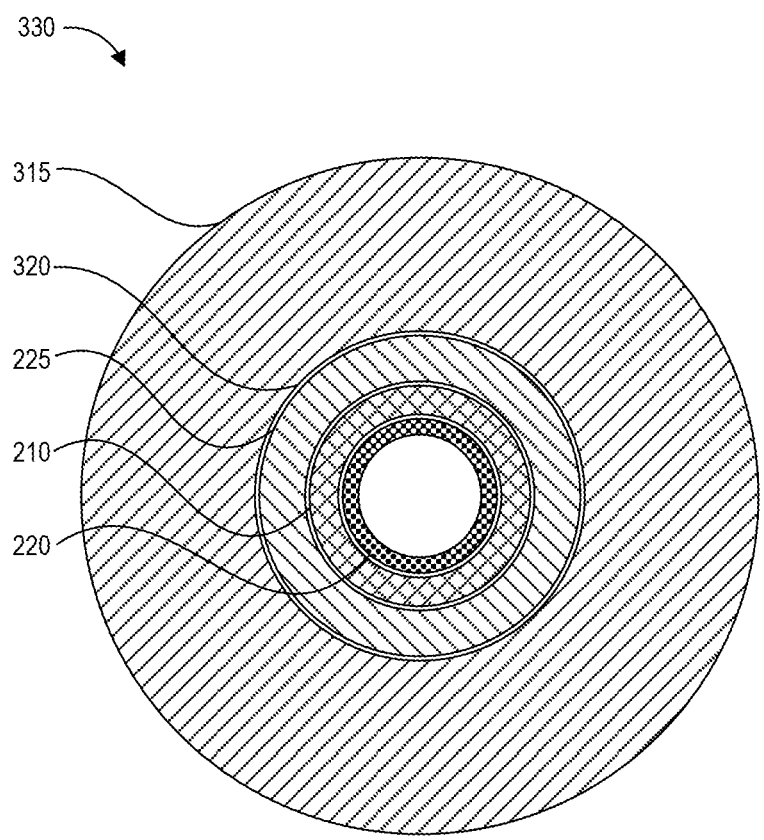
FIG. 3C depicts a cross-sectional view of the scope, jacket, tube, and needle of FIGS. 3A and 3B.

Medical procedures may involve manipulation of a tool positioned remotely from the operator, for example, positioned through a channel (e.g., trocars, catheters, endoscopes, etc.) inserted into the body of a patient. As one example of such a procedure, transbronchial needle aspiration (TBNA) can be used as a minimally invasive bronchoscopic technique for diagnosis and staging of bronchial diseases, including lung cancer. A TBNA technique can involve manipulating a biopsy needle through a flexible bronchoscope. For example, a physician can use chest scans to identify the location of a mass to be biopsied and to guide positioning of the bronchoscope within the patient's airways towards that mass. After the distal end of the bronchoscope working channel is positioned within the airways near the identified mass, an elongate, tubular jacket containing the biopsy needle can be advanced through the working channel to the sampling area. The target tissue can then be pierced by extending the needle out of the jacket, and aspiration can be applied to aid sample acquisition. Typically, sample acquisition involves moving the tube backward and forward relative to the bronchoscope to repeatedly puncture the tissue site with the needle (referred to as "dithering"). After sample acquisition, the needle can be retracted back into the jacket and withdrawn through the working channel. In some procedures, sample analysis can be performed in the same room and/or contemporaneously as the TBNA procedure, and depending upon results of the analysis further TBNA sample acquisition, other tissue sampling, and/or treatment can be performed.

Bronchoscopy techniques including TBNA can involve challenges accessing masses at the periphery of the lungs, particularly if such masses are relatively small, for example, around 8 mm or smaller. Sampling masses at the periphery presents challenges in diagnosing and staging cancerous masses, particularly in early cancer stages, a timeframe during which such masses may be more easily treatable and may not have spread to other places in the patient's body. For example, a challenge in using a needle with a flexible bronchoscope is that the needle ought to be flexible enough to be maneuverable through the tortuous pathways of the bronchoscope to the target tissue site while also being rigid enough to deploy straight and allow penetration of the target tissue, and further that the needle preferably deploys in a straight trajectory over a distance sufficient to reach the lung periphery.

With respect to flexibility, bronchoscopes are increasingly minimizing the bend radiuses that they can achieve to allow the bronchoscopes to navigate through patient airways. With respect to rigidity, a bronchial wall or tumor tissue may present significant resistance to penetration by the needle. Some previous approaches use a short, rigid needle at the distal end of a plastic sheath to address these requirements so that the needle does not have to bend much as it travels through the bronchoscope. One example of an existing needle is a rigid needle approximately 7 mm or less in length (see for example needle 450 in FIG. 4B). However, using this relatively short needle limits the extent to which the needle can be deployed straight—that is, the ability of the needle to be extended from the working channel with a proximal end still secured within the working channel. This can limit the range of the needle, preventing sampling of tissue at or near the periphery of the lungs. Further, the sheath cannot penetrate the tissue and thus causes trauma to patient tissue if it is jammed into the tissue, deflecting the tissue in order to allow for deeper penetration by the needle.

The aforementioned challenges, among others, are addressed in some embodiments by the superelastic needle assemblies described herein. Embodiments of the disclosure relate to superelastic needles, and specifically to needles that are pre-formed into a shape (e.g., straight or curved), capable of bending elastically through the tortuous pathways of a bronchoscope, returning to the pre-formed shape upon deployment from the bronchoscope, and deploying along the axis of the end of the bronchoscope (within a tolerated margin) with improved reach (e.g., in some embodiments, up to distances of 2 cm or more). The disclosed superelastic needles are configured for increased stability and accuracy during deployment by maintaining overlap between a proximal portion of the needle, a distal end of a scope used to deliver the needle, and a distal end of a jacket containing the needle within the scope. The increased length of the disclosed needle allows for this overlap while still achieving the needed reach, and the disclosed superelastic alloys enable the increased needle length to pass through curvatures of the scope. Further, the disclosed needle reduces scope tip deflection at the tip of the scope during the delivery of the needle through the working channel, which provides the desired accuracy in tissue sampling. In addition, the disclosed needle has aspiration/negative and/or positive pressure capabilities by having an open interior lumen. Thus, the disclosed needles can provide enhanced ability to sample tissue at the periphery of the lungs, for example, smaller lesions. Beneficially, this can allow a physician to diagnose and stage small, peripheral cancerous masses in earlier stages.

The disclosed systems and techniques can provide advantages for bronchoscopic needle biopsies and other applications, including manipulation of other endoscopic, laparoscopic, and/or catheter-delivered tools. For example, a superelastic shaft similar to the disclosed needle can be provided for other types of medical tools, for example, augers, cytology brushes, and/or forceps. It will be appreciated that the needle dimensions described below could be similarly applicable to the dimensions of a superelastic shaft, and that the superelastic shaft may or may not be formed as a tubular shaft with an interior lumen. Thus, though the disclosed superelastic shafts are described in portions of the present disclosure below within the context of bronchoscopy biopsy needles, it should be understood that such shafts can also be used with other endoscopic tools and in other types of procedures in order to provide the disclosed benefits. For example, a superelastic medical tool as described herein can be used in other types of procedures including laparoscopy, gastrointestinal endoscopy, urethroscopy, cardioscopy, and other procedures delivering tools through flexible and/or curved scopes, catheters, or tubes (collectively referred to as endoscopes, for simplicity of describing the various embodiments discussed herein).

As used herein, the term "superelastic" generally refers to a mechanical type of shape memory in which an elastic (reversible) response to an applied stress is caused by a solid-solid phase transition. In some cases, superelastic effects are induced when a crystalline material in an austenite state is mechanically loaded up to a critical stress and within a specific temperature range above the martensitic transformation finishing temperature, at which point a phase transition to the martensite phase is induced. When so mechanically loaded, a superelastic material can deform reversibly to very high strains (for example, with Nitinol up to 10%) by the creation of such a stress-induced phase. When the load is removed, the martensite phase becomes unstable and the material undergoes the reverse deformation to regain its original shape. Further, no change in temperature is needed for the material to undergo this reverse deformation and recover this initial shape. Nitinol is a metal alloy of nickel and titanium that exhibits superelastic properties in a range of temperatures around room temperature. Other examples of superelastic materials include alloys of nickel and titanium with other elements (Ni—Ti—Fe, Ni—Ti—Cr, Ni—Ti—Cu—Cr), some polycrystalline ferrous alloys (e.g., Fe—Ni—Co—Al—Ta—B and Fe—Mn—Al—Ni), Cu—Al—Mn (CAM) alloys, and Cu—Zn—Sn alloys. It is to be appreciated that although the disclosed superelastic materials may be discussed herein with respect to implementation as a needle that is formed in, and reverts to, a straight shape, it will be appreciated that a medical tool formed from the disclosed superelastic materials can be formed to revert to a curved, angled, or otherwise non-straight shape in other implementations.

As used herein, strain generally refers as the amount of deformation an object experiences compared to its original size and shape and can be expressed as a percentage.

As used herein, "distal" refers to the end of the scope or tool positioned closest to the patient tissue site during use, and "proximal" refers to the end of the sheath or tool positioned closest to the operator (e.g., a physician or robotic control system). Stated differently, the relative positions of components of the jacket, needle, and/or the robotic system are described herein from the vantage point of the operator.

As used herein, the term "dithering" refers to a back and forth motion of a medical instrument such as a biopsy needle, for example during tissue sampling. The dithering movement of the needle can be independent of the movement of the needle's jacket such that the jacket of the needle remains relatively stationary during the dithering.

As used herein, the term "approximately" refers to a range of measurements of a length, thickness, a quantity, time period, or other measurable value. Such range of measurements encompasses variations of +/10% or less, preferably +/−5% or less, more preferably +/−1% or less, and still more preferably +/−0.1% or less, of and from the specified value, in so far as such variations are appropriate in order to function in the disclosed devices, systems, and techniques.

Robotic surgical systems can utilize endoscopic instruments to perform minimally invasive endoscopic procedures robotically. Thus, some implementations of the disclosure relate to surgical instruments and systems that include superelastic needles that can advantageously be used in robotically-guided (whether fully automated robotic systems or robotic systems that provide some level of assistance) medical procedures, and methods of performing a medical procedure under guidance of a robotic surgical system. In such systems, a robotic arm can be configured to control the extension, dithering, and/or retraction of needles as described herein. Drive signals for such actuation can be supplied by the robotic surgical system, for example, in response to user input via an input device and/or computer-controlled surgical processes.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

Overview of Example Needle Assemblies

FIGS. 1A and 1B illustrate an embodiment of a superelastic needle 120 as described herein. FIG. 1A shows the two components of the needle assembly 100, the superelastic needle 120 and an elongate shaft 110 coupled to the needle 120.

The needle 120 is formed as a thin-wall tube. The needle 120 is capable, in some embodiments, of delivering negative (or positive) pressure through an interior lumen (not illustrated), the lumen extending through the body of the needle 120 from a first aperture 121 at its proximal end to a second aperture 124 at its distal end 125. In some embodiments the needle has a wall thickness of approximately 0.0015 inches. This thin wall can add to the flexibility of the needle and also beneficially increase the interior diameter of the needle to collect greater amounts of biopsy material. The outer diameter of the needle can be up to 0.023 inches in some implementations, as for larger diameters, the wall may need to be impractically thin to maintain the desired flexibility. Smaller outer diameters can have thicker walls, however the interior lumen of such needles would be able to collect less material. It is to be appreciated that these measurements are provided to possible embodiments and do not limit the scope of other embodiments contemplated by this disclosure.

The needle 120 can be formed from Nitinol in some implementations, though, in other implementations, one or more other suitable superelastic materials can be used. Nitinol is a nickel-titanium alloy with approximately equal parts nickel and titanium by atomic percent, for example having a nickel to titanium ratio between 0.92 and 1.06. In some embodiments formed from Nitinol, the superelastic material of the needle 120 can assume an interpenetrating simple cubic structure (referred to as the austenite phase) and can be set in this phase in the straight, tubular shape shown in FIG. 1A. When Nitinol in the austenite phase is subject to exterior forces in a temperature range from about −20° C. to +60° C., the Nitinol can undergo a phase transformation to the martensite phase as well as changing shape (e.g. to bend along its longitudinal axis as it travels through a bronchoscope). In the martensite phase, the crystal structure of the Nitinol shifts to a monoclinic structure, giving it the ability to undergo twinning deformation (e.g., the rearrangement of atomic planes without causing slip, or permanent deformation) without breaking atomic bonds. The Nitinol can reversibly undergo up to 10% strain in this manner. Upon release of the strain, the Nitinol automatically reverts back to the austenite phase and the original shape. In superelastic Nitinol, this reversion occurs without the requirement of any temperature change, as opposed to shape memory Nitinol.

In other implementations, one or more other suitable superelastic materials capable of the austenite-martensite, solid-solid phase transformation can be used to form the needle 120. As described above, such materials include other alloys of nickel and titanium with other elements (Ni—Ti—Fe, Ni—Ti—Cr, Ni—Ti—Cu—Cr), some polycrystalline ferrous alloys (e.g., Fe—Ni—Co—Al—Ta—B and Fe—Mn—Al—Ni), Cu—Al—Mn (CAM) alloys, and Cu—Zn—Sn alloys. Thus, the needle 120 can be formed from superelastic materials having (1) a first solid crystal structure set to a straight, tubular shape in its austenite phase, (2) a second solid crystal structure that allows elastic deformation (e.g. bending) of the tubular shape up to a threshold strain percentage in its martensite phase, and (3) the capability to automatically revert from the martensite phase back to the austenite phase (and thus the original straight, tubular shape) upon release of the strain and without requiring any temperature change.

The elongate shaft 110 can be formed as a tube having an aperture 104 at its proximal end 102 leading to an interior lumen 106 that is in fluid communication with the lumen of the needle 120. Aspiration or positive pressure can be applied through the aperture 104 and delivered through the distal aperture 124 of the needle 120. The elongate shaft 110 can be a flexible thermoplastic polymer, for example a flexible polymeric single lumen extrusion formed from HDPE (high density polyethylene). Other flexible thermoplastics can be used in other embodiments, alone or in a blend or layered combination. For example, multiple polymers could be reflowed together to create a tube that is stiffer at one end and more flexible at the other end. In some implementations, the elongate shaft 110 can be formed from braided wire with a heat shrink to provide some torqueing capability to the wire.

The elongate shaft 110 is secured to the needle 120 at the overlap region 130. This can be a fluid-tight (e.g., air tight and liquid tight) connection in some implementations. In order to secure the elongate shaft 110 to the needle 120, in some examples of the elongate shaft 110 can be reflowed around the needle 120 at an overlap region 130. For example, a mandrel can be placed inside of the lumen of the needle 120 and the lumen 106 of the elongate shaft 110 and the elongate shaft 110 can be positioned around the needle 120 in the overlap region 130. The mandrel can help ensure that the lumen does not become occluded during the reflow process. Heat shrink can be positioned around the elongate shaft 110 and needle 120 at least at the overlap region 130 and heat applied to melt the material of the elongate shaft 110, causing it to reflow around and bond to the exterior surface of the needle 120. The exterior surface of the needle 120 may have surface features along some or all of this overlap region 130 to promote a better bond, for example a grit blasted or sanded surface, laser cut etching or through-holes, or surface etching or holes formed by other drilling and/or cutting techniques. In some embodiments, the polymer elongate shaft 110 can have a cone-shape at its distal end prior to and/or after the reflowing. The cone shape can provide a ramp up or smoothening of the transition from needle to tube.

In other embodiments, the elongate shaft 110 and needle 120 can be bonded in other ways alternative to or additional to the reflowing described above. For example, the wall of the needle 120 can be provided with etched, molded, or cut features (e.g., barbs, spiral channels, and the like) and the proximal end of the elongate shaft 110 can be etched, molded, or cut to have corresponding features that mate with and lock into the barbs in the needle 120. As another example, the elongate shaft 110 could have additional lumens within a portion of the wall and barbs extending from the needle 120 could be positioned within these additional lumens and secured via adhesive, mechanical mating elements, and/or reflowing. In other examples mechanical fasteners (e.g., pins, screws, etc.) or flexible adhesives (e.g., silicone adhesives) can be used to couple the elongate shaft 110 and needle 120. Further, in some implementations the elongate shaft 110 can be connected directly to the proximal end of the needle such that no overlap region is included. Other approaches can use a die bonding where two heated plates perform the reflow.

In one example design, it is desired for the needle 120 to be able to deploy straight across a distance of at least 3 cm. For example, a scope with which the needle 120 can be used may be able to get difficult to reach nodules, as some endoscopes can reach within 3 cm of most areas of the lung. Further, reach of this length gives the practitioner different options for how a scope is positioned to obtain a biopsy. Thus, the needle can have a length of at least 3 cm in some embodiments. In other embodiments, the needle can be longer, for example 5 cm to 6 cm, in order to provide an "anchor" portion that remains within the scope during extension of the distal tip 125 up to 3 cm. This can beneficially provide stability for straight deployment of the needle to the target tissue site. Accordingly, in various embodiments, the overlap region 130 can be 2-3 cm long and can form the anchor portion intended to remain within the working channel of the scope, and the portion of the needle 120 extending distally beyond the overlap region 120 can be approximately 3 cm to 4 cm long.

Some endoscopic procedures may involve using fluoroscopy to assist with navigation of medical instruments through patient luminal networks. In fluoroscopy, a source of x-ray radiation is provided to pass an x-ray beam through patient tissue. This beam can be received by a screen positioned on the other side of the patient from the x-ray radiation source, and the resulting signal can be used to generate images (e.g., in grayscale or false color) to depict the internal structure of the patient. Radiopacity refers to the relative inability of electromagnetic radiation, particularly X-rays, to pass through a particular material. Materials that inhibit the passage of X-ray photons are referred to as radiopaque, while those that allow radiation to pass more freely are referred to as radiolucent or radio-transparent. The term "radiopaque", as used herein, generally refers to the relatively opaque, white appearance of dense materials viewed in radiographic imaging, compared with the relatively darker appearance of less dense materials. Nitinol and some other superelastic materials can be radio-transparent or radiolucent, making these materials invisible or near-invisible when viewed in x-ray photographs or under fluoroscopy. This can make navigation of the needle 120 through a patient difficult when using fluoroscopy-based navigation systems.

Accordingly, some embodiments of the needle 120 can be provided with a radiopaque material 123 near the sharpened tip and distal end 125. In some examples, the radiopaque material 123 can be positioned around 3 mm from the distal tip of the needle 120. As described above, radiopaque materials are opaque to x-ray radiation and thus visible in x-ray photographs and under fluoroscopy. As such, although the material of the needle 120 may be radio-transparent, its navigation can be guided by observing the position of the radiopaque material 123. Providing the radiopaque material 123 near the distal end 125 (or as close as possible to the distal end 125 given the tapered or sharpened tip) can beneficially provide an indication of how close the distal end 125 is to the target tissue site.

In one example, this radiopaque material 123 can be formed as a thin gold band and secured around the exterior surface of the needle 120. Generally, elements with higher atomic numbers have higher radiopacity, and thus radiopacity of a material increases alongside an increase in the particle ratio of those materials which have an element content with a high atomic number. Other implementations can use suitable radiopaque materials having high element content of elements with high atomic numbers, including tungsten, precious metals and alloys containing precious metals including chromium-nickel alloys (Cr—Ni), radiopaque ceramics, and radiopaque thermoplastics. In some embodiments the radiopaque material 123 can be formed as a number of blades to increase flexibility. Preferably, the selected radiopaque material is sterilizable and non-toxic to human tissue. It will be appreciated that other shapes and positions can be used for the radiopaque material 123 besides the illustrated band, for example by providing surface etchings or holes in the needle 120 and filling such etchings or holes with the radiopaque material 123. In some embodiments the radiopaque material 123 may be secured to the interior of the needle 120.

As shown in FIG. 1B, the needle 120 is formed with a sharpened tip 140 at its distal end 125. The sharpened tip 140 includes a lancet design where one zone 144 is ground flat at a first angle and a second zone 142 is ground flat at a different angle. The second zone 142 provides a linear slope to the end of the sharpened tip 140 that meets the full diameter of the needle 120. The diameter of the needle 120 increases again at the location of the radiopaque material 123.

As a first force, $F_i$, reflects the initial puncture force required to drive the tip of the needle 120 into the patient tissue. This force can increase along the region of the sharpened tip 140, reaching a peak puncture force $F_p$ at the full diameter of the needle 120. Another increase in puncture force to the collar passage force $F_c$ can occur when inserting the leading edge of the radiopaque material 123 into the tissue.

It will be appreciated that the thickness of the radiopaque material 123 has implications for both radiopacity and an increase in the puncture force required to insert the increased thickness into patient tissue. In various embodiments using a gold band, the wall of the gold band can have a thickness in the range of 500 pin (micro-inches) to 1000 pin to achieve a desired balance between these factors. Some embodiments can use a radiopaque material 123 having a thickness of at least 200 pin.

FIGS. 2A-2C illustrate various configurations of a needle assembly 200 as described herein. The needle assembly 200 includes needle 220, shaft 210 coupled to the needle 220 at overlap region 215, and jacket 225. The needle 220 and shaft 210 can be the needle 120 and elongate shaft 110 discussed above with respect to FIG. 1. As depicted, the needle 220 includes a radiopaque material 230 secured near the distal tip 240. The jacket 225 can be a polymer catheter or tube in some embodiments, and in other embodiments can be a steerable channel. The outer diameter of the jacket 225 can be selected to substantially match the interior diameter of the working channel of a scope for secure centering of the needle 220 relative to the working channel. The jacket 225 can include a band of radiopaque material at or near its distal tip.

FIG. 2A illustrates the needle assembly 200 in a retracted configuration 205A. In the retracted configuration 205A, the distal end 240 of the needle 220 is positioned at or proximally to the distal end 235 of the jacket 225 and the jacket 225 surrounds the depicted portion of the tubular shaft 210. However, a proximal end of the shaft 210 may extend beyond a proximal end of the jacket 225 so that it can be moved relative to the jacket 225 to extend the needle 220 through the distal aperture 245 of the jacket 225 into the other configurations discussed below. The lumen 205 of the shaft 210 extends through the jacket 225. In some embodiments, a fully retracted configuration can have the distal end 240 of the needle 220 positioned a certain distance within the jacket 225, for example 5 mm from the distal end 235 of the jacket 225. As shown in FIG. 2A, the overlap region 215 can help position the needle 220 centered relative to the jacket 225.

FIG. 2B illustrates the needle assembly 200 in a partially-extended configuration 205B. The distal end 240 of the needle 220 is positioned distally beyond the distal end 235 of the jacket 225 in the partially-extended configuration 205B with the shaft 210 positioned within the aperture 245 of the jacket 225. The needle 220 can be driven from the retracted configuration 205A to the partially-extended configuration 205B by distal movement of the shaft 210.

FIG. 2C illustrates the needle assembly 200 in a fully-extended configuration 205C. The exposed portion 250 of the needle 220 (e.g., the portion positioned distally from the overlap region 215 is positioned distally beyond the distal end 235 of the jacket 225 in the fully-extended configuration 205C with the overlap region 215 of the shaft 210 positioned at least partially within the jacket 225. In some embodiments, the exposed portion 250 of the needle 220 can be positioned flush with the jacket 225, that is, a distal edge 245 of the overlap region 215 can be positioned at the distal end 235 of the jacket 225. As shown in FIG. 2C and as discussed in greater detail below relative to FIG. 3C, the overlap region 215 can help the needle 220 to remain centered in the jacket 225, and thus centered and anchored in the working channel of a scope with the jacket 225 positioned within the scope, even when the full exposed length 250 of the needle is extended beyond the distal end 235 of the jacket. The needle 220 can be driven from the partially-extended configuration 205B to the fully-extended configuration 205C by distal movement of the shaft 210, and can be driven from the fully-extended configuration 205C to the partially-extended configuration 205B by proximal movement of the shaft 210.

As described above, in some embodiments the distal tip 240 of the needle 220 can extend 3 cm, or in the range of 2 cm to 4 cm, beyond the distal end 235 of the jacket 225 in the fully-extended configuration 205C. The length of the needle 220 can be between 1 cm to 6 cm. The overlap region 215 can overlap a distance of 0.5 cm to 3 cm from the proximal end of the needle 220. One example needle has an overlap region 215 length of around 1 cm and an exposed needle length of around 2 cm. Another example needle has an overlap region 215 length of around 2 cm and an exposed needle length of around 3 cm. Another example needle has an overlap region 215 length of around 2 cm and an exposed needle length of around 4 cm. It will be appreciated that longer needles, while providing a greater ability to sample lesions further from the distal tip of a scope, may have reduced ability to traverse the tortuous passages of the scope. It is to be appreciated also that the dimensions provided above are merely exemplary and other dimensions may be suitable depending on application and design requirements of the needle assembly.

FIGS. 3A and 3B illustrate the needle assembly 200 of FIGS. 2A-2C exhibiting superelastic properties in retracted and extended configurations. FIG. 3A illustrates the needle assembly 200 in a martensite state 300A with the needle assembly 200 positioned within the working channel 320 of a scope 315, illustrated in cross-section to reveal the needle assembly 200. The needle 220 can be positioned with its distal tip 240 within the jacket 225. The jacket 225 and needle 220 can be advanced together through working channel 320 of the scope 315 until the distal end 235 of the jacket 225 and the distal end 240 of the needle 220 are positioned at (or near) the distal end 325 of the scope 315.

As described above, in the martensite state 300A the needle is able to undergo strain up to a certain threshold while deforming reversibly. As illustrated, the needle 220 has two bends along its longitudinal axis. As an example, the needle 220 can bend around a radius of curvature a while deforming reversibly in the martensite state 300A. In one example, the needle 220 can be around 5 cm in length with a 0.0015 inch thick wall, and can elastically bend around a radius of 9-12 mm or greater. Some examples of the needle 220 can deform elastically around 180 degree bends. This deformation can occur repeatedly as the jacket 225 containing needle 220 is inserted through the working channel of a scope.

FIG. 3B illustrates the needle assembly 200 in deployment 300B. As illustrated, the assembly 200 has a portion 305 of the needle 220 still positioned within the jacket 225. Of this portion 305, a portion is still deformed around the radius of curvature a in the martensite state. The assembly 200 also has a portion 310 of the needle 220 that has been "deployed," that is, extended beyond the distal end 235 of the jacket 225. The deployed portion 310 is no longer subject to strain due to the bend of the jacket 225 and, as a result, has returned to the austenite phase and thus has straightened. Beneficially, this automatic reverse deformation allows the needle 220 to traverse tight bends through a scope and still deploy substantially straight along the longitudinal axis extending out of the scope working channel. Such deployment increases accuracy with respect to sampling pre-identified target tissue regions.

Further, increased stability and accuracy during deployment of the needle as illustrated in FIG. 3B can be achieved by maintaining example portion 305 of the needle 220, shaft 210, and jacket 225 within the working channel 320 of the scope 315. Though FIG. 3B depicts a specific length of overlap of the needle 220, shaft 210, and jacket 225 within the working channel 320, it will be appreciated that any overlap of these components achieves the desired stability by securely centering the needle 220 in the working channel 320. For example, FIG. 3C depicts a cross-sectional view 330 of the scope 315, jacket 225, shaft 210, and needle 220 that illustrates the stability-increasing configuration along portion 305 of FIG. 3B. As illustrated, the outer surface of the jacket 225 contacts and is supported by the working channel 320 of the scope 315, the inner surface of the jacket 225 contacts and supports the outer surface of the shaft 210, and the inner surface of the shaft 210 contacts and supports the outer surface of the needle 220 (e.g. at overlap region 215). This arrangement centers the needle 220 relative to the working channel 320, increasing accuracy during deployment. It will be appreciated that the gaps shown between the components in FIG. 3C are for clarity of illustration, and the overlapping configuration can be structured without gaps in various implementations. Further, the working channel 320 can be centered relative to the scope 315 as illustrated or may not be centered in other embodiments.

Figure 4A:
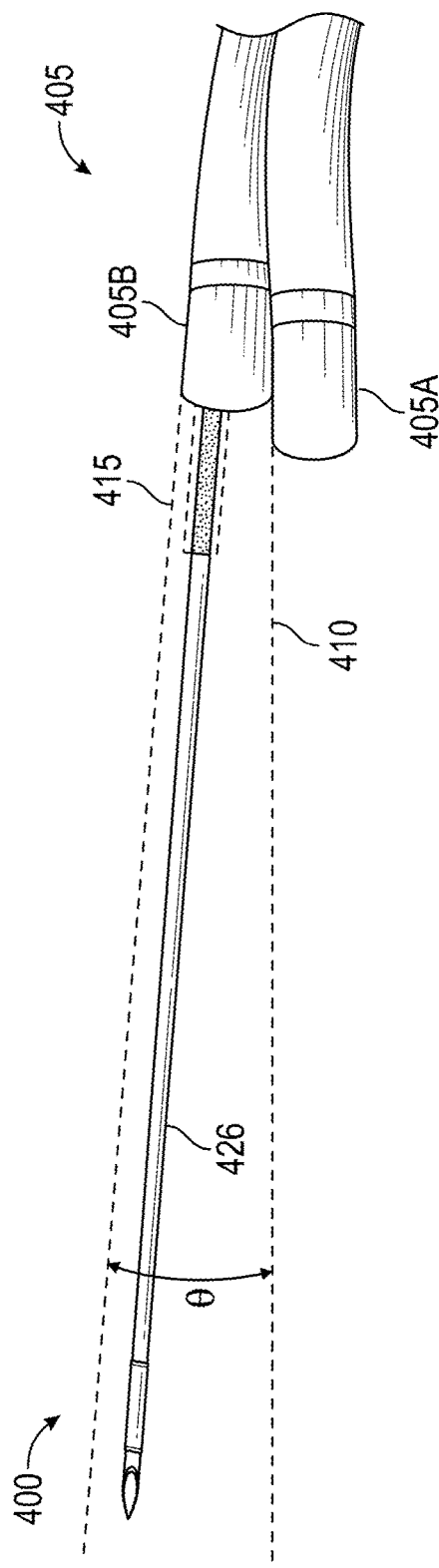
FIG. 4A illustrates an example offset angle comparison between scope axes before and after passage of a superelastic needle through the scope.

FIG. 4A illustrates an example offset angle comparison 400 between scope axes 410, 415 before and after passage of a superelastic needle 420 through the scope. The needle 420 can be the needle 120, 220 described above and the jacket (not depicted) is located within the working channel of the scope 405. The depiction of FIG. 4A shows the distal end of a scope 405 in two positions 405A, 405B each from one of two images overlaid onto one another to produce the offset angle comparison 400. In a first image taken before insertion of needle 420 through the scope, the distal end of the scope 405 is in an undeflected position 405A with a portion of the scope proximal to the distal tip actuated into a curve. In a second image taken after deployment of the needle 420 through the scope 405B, the distal end of the scope 405 is in a deflected position 405B. A dashed line representing an undeflected axis 410 is depicted parallel to and extending from the distal end of the scope 405 in the undeflected position 405A, and a dashed line representing a deflected axis 415 is depicted parallel to and extending from the distal end of the scope 405 in the deflected position 405B. These axes are offset by an angle $\theta$. It is to be noted that these illustrated deflections are experienced in air but may experience less deflection in the patient site. For example, while in the body, the surrounding tissue may restrict movement of the scope or the deflection may cause the surgical site to move relative with it.

In the example shown in FIG. 4A, the "spring" force of the superelastic needle 420 attempting to revert to its straightened original shape through the curve deflects the distal end of the scope at an angle $\theta$ of 5.6 degrees. In another example scope, this angle is reduced to 2 degrees. In some implementations, an allowable deflection of the scope tip due to needle deployment can be plus or minus ten degrees and still allow accurate sampling of target tissue sites. To illustrate, consider that the working channel of the scope 405A is positioned such that the target tissue site is viewable via optics at the distal tip of the scope. Based on the size of the target lesion and its distance from the distal tip of the scope 405, the angle of the needle longitudinal axis after deflecting the scope tip (parallel to the deflected axis 415) can be offset from the undeflected axis 410 within a certain range and the distal tip of the needle 420 will still puncture the target lesion.

In some embodiments the scope 405 is steerable, and the deflection can change the values of tension upon various pull wires or actuating cables within the scope 405. A robotic control system, for example as discussed in more detail below with respect to FIG. 6, can sense this change in tension and use this to compensate for the deflection of the scope by applying greater tension or force to certain pull wires or actuation cables. Some control system implementations may compensate for tension changes to keep the scope as close as possible to its undeflected position 405A. Other control system implementations may compensate for any tension changes outside of a predetermined range corresponding to an angle of deflection $\theta$ that exceeds an allowable angle for sampling the target tissue site. Alternative to an automatic control approach, other embodiments may correct deflection based on physician adjustments to the scope.

Figure 4B:
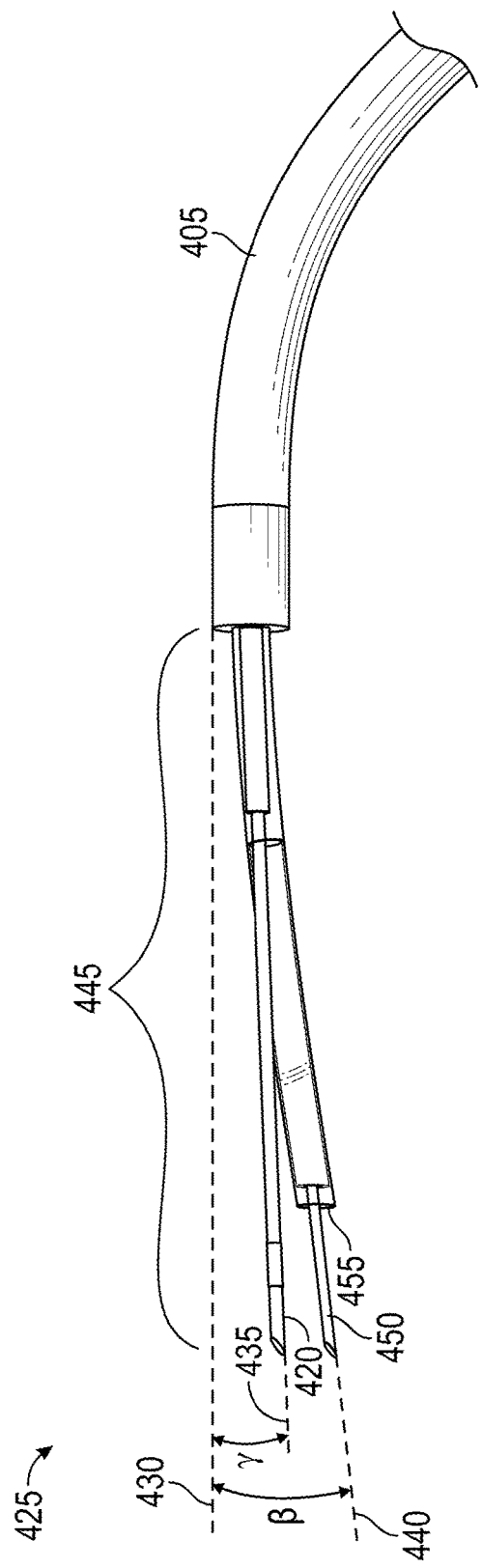
FIG. 4B illustrates a deflection angle comparison between the disclosed superelastic needle and a conventional needle deployed out of the scope to the same distance.

FIG. 4B illustrates a deflection angle comparison 425 between the disclosed superelastic needle 420 and a conventional needle 450 deployed out of the scope 405, where both needles are deployed to the same distance 445 from the distal end of the scope. The conventional needle 450 is a short (e.g., up to 7 mm) stainless steel tube secured to a conduit 455. The distance 445 in the present example is 4 cm from the tip of the scope 405. The deflection angle comparison 425 involved extending both needles 420, 445 from the same scope 405 having the same undeflected position, capturing an image of each extended needle, and then overlaying the images to illustrate the comparison 425.

A dashed line representing an axis 430 of the scope 405 is depicted parallel to and extending from the distal end of the scope 405. A dashed line 435 representing an axis of the needle 420 of the present disclosure is depicted extending from the needle 420. A dashed line 440 representing an axis of the conventional needle 450 is depicted extending from the needle 450. As illustrated, the axis 440 of needle 450 is offset from the scope axis 430 by an angle $\beta$, and the axis 435 of needle 420 is offset from the scope axis 430 by an angle $\gamma$. In the depicted example angle comparison 425, the offset angle $\beta$ between the axis 440 of needle 450 and the scope axis 430 is equal to 8.1 degrees and the offset angle $\gamma$ between the axis 435 of needle 420 and the scope axis 430 is equal to 1.8 degrees, plus or minus about 0.5 degrees. Thus, the disclosed superelastic needle 420 exhibits reduced deflection compared to the conventional needle 450.

Figure 5:
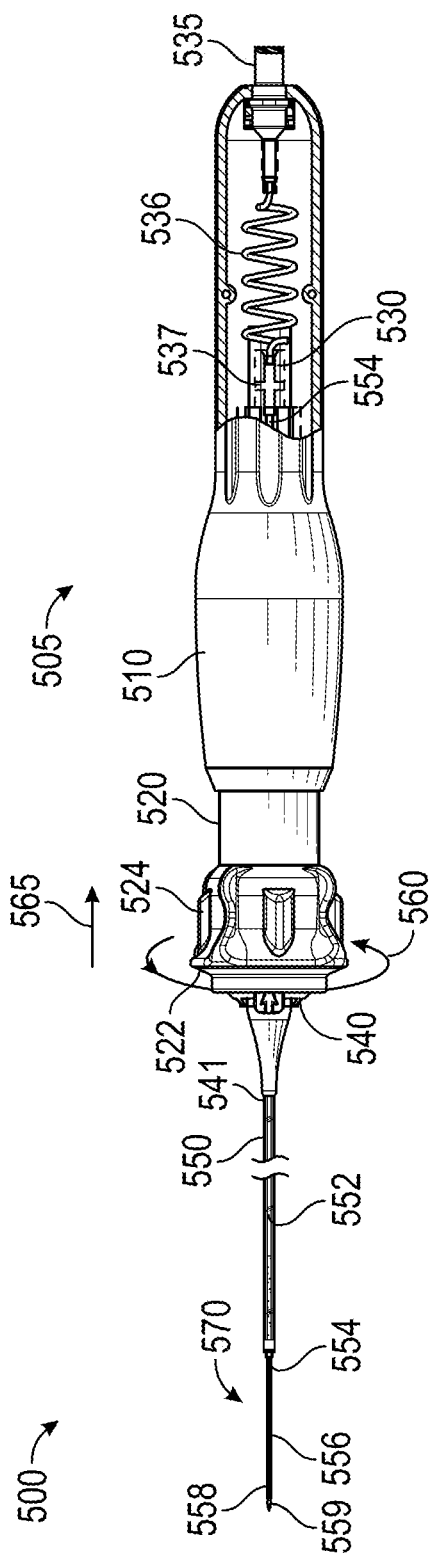
FIG. 5 illustrates an embodiment of a needle assembly as described herein including an example manipulating handle.

FIG. 5 illustrates an embodiment of a needle assembly 500 as described herein coupled to an example manipulating handle 505. The needle assembly 500 includes a needle 556, an elongate shaft 554 (e.g., a polymer tube) bonded or otherwise secured to needle 556, a jacket 550 positioned at least partly around the shaft 554 and needle 556, and a handle 505. In the view of FIG. 5, a portion of the handle 505 is shown cut away to reveal interior components.

The needle 556 can be formed from a superelastic material, for example Nitinol, and bonded to the polymer tube via reflowing over an overlap region as described above. The needle 556 can be the needle 100, 220, 420, the shaft 554 can be the elongate shaft 110, 210, and the jacket 550 can be the jacket 225 in various embodiments. As illustrated, the jacket 550 extends from a distal aperture 541 of the handle 505 through a strain relief, and can contain some or all of the shaft 554 and needle 556 in various configurations. The shaft 554 has an interior lumen 552 that provides at least a portion of a fluid pathway between a proximal aperture of the fluid coupling 535 of the handle 505 and the distal end 559 of the needle 556. The needle 556 can be a biopsy needle such as an aspiration needle configured for acquisition of tissue samples or can be configured for delivery of therapeutic agents to a tissue site, and can be provided with a band 558 of radio-opaque material near the distal end 559.

The handle 505 includes casing 510, actuation sleeve 520, driving member 530, and fluid fitting 535. Various examples of the handle 505 and other handles suitable for actuating movement of the disclosed superelastic medical tools are described in U.S. application Ser. No. 15/937,516, entitled "SHAFT ACTUATING HANDLE," filed Mar. 27, 2018, the disclosure of which is hereby incorporated by reference. The driving member 530 can be driven linearly along a longitudinal axis of the handle 505 by various motion modalities of the actuation sleeve 520, as described in more detail below. The shaft 554 attached to needle 556 can be secured within a recess 537 of the driving member 530, for example by bonding via an adhesive. Thus, linear motion of the driving member 530 can transfer to the needle 556 via the shaft 554, allowing manipulation of the handle 505 to drive extension and retraction of the needle 556 from jacket 550. In some embodiments the recess 537 can be structured to mechanically mate with a corresponding feature on the shaft 554 to facilitate use of the handle 505 with a number of different conduits and tools. Thus, in some embodiments the handle 505 may be sterilizable and reusable while the conduit, needle, and jacket may be disposable. In various other embodiments the entire instrument 500 may be entirely sterilizable and reusable or designed as a disposable single unit.

The actuation sleeve 520 can have a rotational wheel grip 524 and a plunger grip 522 to facilitate its actuation by an operator. The operator can drive motion of the needle 556 relative to the jacket 550 by rotating 560 the rotational wheel grip 524, which causes rotation of the actuation shaft 520 around the longitudinal axis of the handle 505. Rotation 560 in one direction can cause extension of the needle 556 from the jacket 550. Rotation in the other direction can retract the needle 556 back into the jacket 550. In some embodiments, the needle can initially be positioned in a retracted configuration, for example as shown in FIGS. 2A and 3A, while the jacket 550 is advanced near a target tissue site. The rotation 560 can be used to advance the distal end 559 of the needle out of the jacket 550 in a controlled and/or incremental manner until the distal end 559 is at or puncturing the tissue. A plunging motion 565 can be driven in one direction by application of force by the operator to plunger grip 522 and driven in the opposite direction in some embodiments by a biasing element upon release of the force. Such a modality can be useful for dithering the needle 556 once extended to the desired distance, for example to acquire a tissue sample.

Actuation sleeve 520 can be coupled to the driving member 530, for example via a cam interface, to transfer these rotational or plunging motions of the actuation sleeve 520 to linear motion of the driving member 530 along a longitudinal axis of the handle 505. Motion of the driving member 530, in turn, is transferred to the needle 556 via the coupling between the shaft 554 and the driving member 530 and the bond between the shaft 554 and the needle 556. Beneficially, during rotation 560 and plunging 565 the fluid fitting 535 may remain stationary with respect to the casing 510 of the handle 505.

Fluid fitting 535 can be a threaded connector for securing to a corresponding threaded connector of an aspiration device, for example a Leur lock. Securing the fluid fitting 535 to the casing 510 can provide benefits in terms of stability of the aspiration device when secured to the fluid fitting 535. Beneficially, during rotation 560 and plunging 565 the fluid fitting 535 may remain stationary with respect to the casing 510 of the handle 505. As shown, a proximal portion 536 of the shaft 554 can comprise a length of coiled tubing in some implementations. This can allow the fluid fitting 535 to be fixed relative to the casing 510 while providing a flexible fluid path that accommodates linear motion of the proximal handle member 530. For example, the proximal portion 536 can be coiled HDPE tubing, and in some embodiments this can be a portion of the shaft 554 positioned proximally from the bonding recess 537. A sleeve of polyolefin heat shrink can be used to secure the coiled tubing to the fluid fitting in some implementations.

The illustrated actuation sleeve 520 and grips 524, 522 represent one example structure for allowing a user to actuate both a fine-control extension and a rapid dithering of the needle 556. In other embodiments, another suitable actuation mechanism can be coupled to the driving member 530, for example a rack and pinion driven by a rotatable wheel provided on the handle 505 or a slidable tab provided on the handle 505. Such alternate actuation mechanisms can be used alone or with a plunger-type dithering interface. Though described in the context of a superelastic needle, in other examples the handle 505 can be used to control other superelastic medical tools as described herein.

Overview of Example Robotic Surgical Systems

Figure 6:
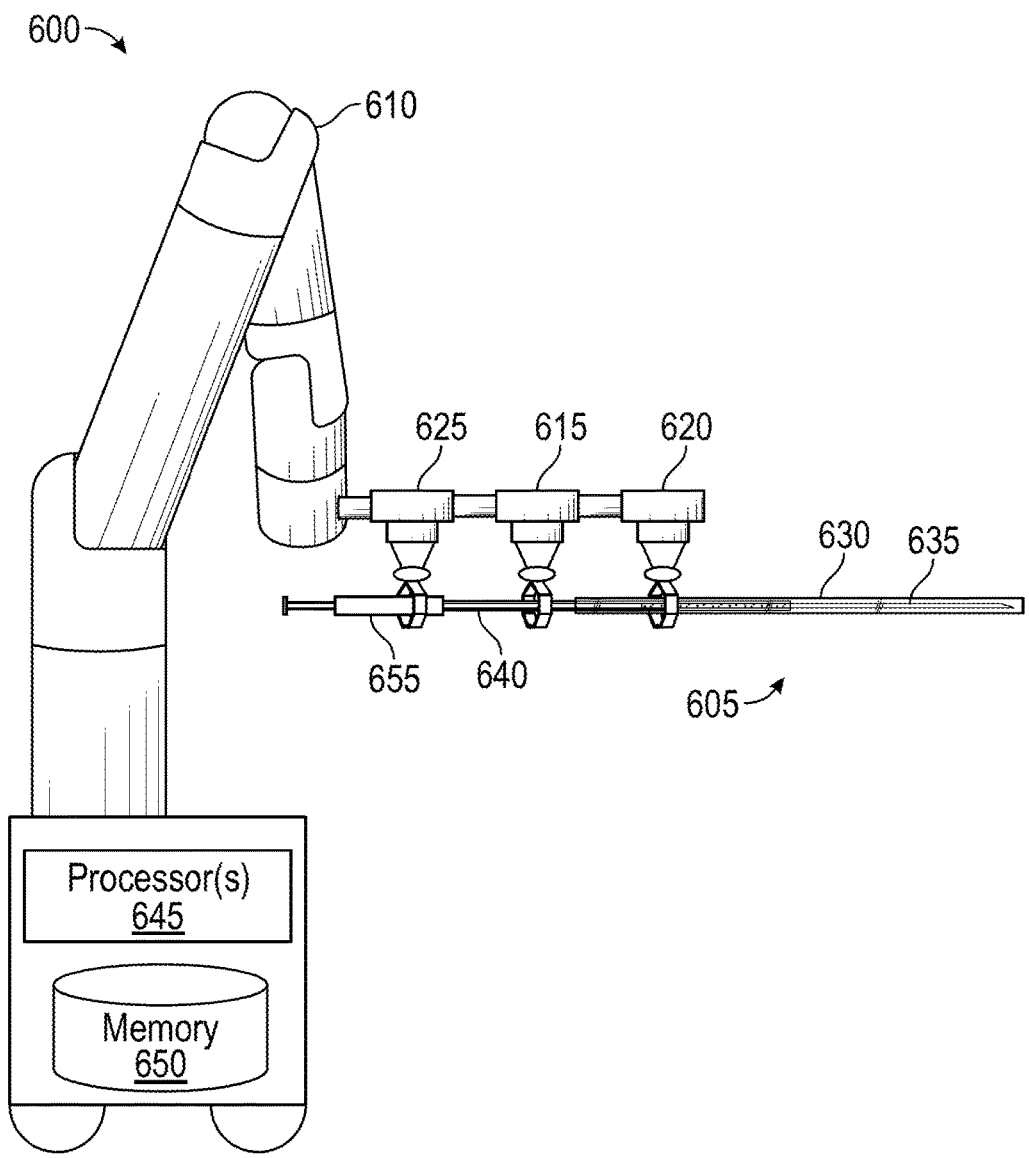
FIG. 6 depicts a schematic diagram of a robotic surgical system for actuating a needle as described herein.

FIG. 6 depicts a schematic diagram of a robotic surgical system 600 for actuating a needle assembly 605 as described herein. The needle assembly includes a jacket 630, needle 635, and a tubular elongate shaft 640 connected to the needle, and can be the needle assembly 200 described above. In other embodiments, the robotic system 600 may instead interface with a handle for manipulating the shaft 640, for example a handle 505 as described with respect to FIG. 5. Other embodiments may interface with support members bonded to proximal ends of the shaft 640 and jacket 630.

The example robotic system 600 includes an articulated arm 610 configured to locate, and maintain positioning of, the needle assembly 605. At a distal end of the arm 610 are a first grip portion 625 for controlling aspiration or administering therapeutics and two additional grip portions 615, 620 that can open to receive and secure the shaft 640 and jacket 630, respectively. The first grip portion 625 can include one or more actuators for gripping and controlling a pressure source 655 of negative (or positive pressure) and/or therapeutics for attaching to the proximal end of the shaft 640. For example, the first grip portion 625 can include a first actuator for attaching pressure source 655, for example a syringe, and a second actuator for robotically controlling a plunger of the syringe. The second grip portion 615 may maintain stationary positioning of the jacket 630. The third grip portion 620 can be configured to move the proximal end of the shaft 640 proximally and distally to move the needle 635 in and out of the jacket 630 and/or to effect a dithering motion as described herein. Other embodiments of the third grip portion 620 can be configured to effect the rotational and/or plunging modality of the handle described herein by rotating a wheel or grip of the handle. The grip portions 615, 620, 625 can be driven by one or more motors and appropriate actuation mechanisms.

The robotic surgical system 600 can include processor(s) 645 and memory 650. The memory 650 can store instructions for operation of the various components of the robotic surgical system 600 as well as data produced and used during a surgical procedure. The processor(s) 645 can execute these instructions and process such data to cause operation of the system 600. One example of instructions stored in the memory of the robotic surgical system 600 is embodied in the tissue sampling method of FIG. 7, discussed below.

For example, the memory 650 can store data relating to the length of a needle and/or overlap region as well as instructions relating to extending the needle from the jacket in order to position the distal end of the needle a desired distance from the distal end of the jacket while maintaining overlap between the needle 220, shaft 210, jacket 225, and working channel 320 of a scope 315 during deployment, for example as shown in FIGS. 3B and 3C. The processor(s) 645 can execute these instructions to cause operation of the system 600 to extend the needle in a stable, accurate manner as described herein. For example, the processor(s) 645 can execute these instructions to cause the robotic system to monitor positioning of the overlap region between the needle and the shaft relative to one or both of the jacket and the working channel/endoscope during or after an extending drive of the needle. In some embodiments, the instructions can prevent the robotic surgical system 600 from driving extension of the needle beyond a predetermined point that would eliminate such overlap. In other embodiments, the instructions can cause the robotic surgical system 600 to provide an alert to an operator of the robotic surgical system 600 when further extension will eliminate such overlap, but may allow the operator to continue driving extension of the needle.

In some embodiments, processor(s) 645 can execute the instructions stored in memory 650 to cause the robotic surgical system 600 to automatically position the scope 315 (prior to or during insertion of a needle assembly 200 through the working channel 320) so that the needle 220 will be able to extend to a target tissue site while maintaining the overlap described herein. Additionally or alternatively, processor(s) 645 can execute the instructions stored in memory 650 to cause the robotic surgical system 600 to output a recommendation regarding such positioning for a user driving endoscope positioning using the system 600. Additionally or alternatively, processor(s) 645 can execute the instructions stored in memory 650 to cause the robotic surgical system 600 to can cause the robotic surgical system 600 to output an alert to the user when the scope has been driven to such positioning.

As described above, deflection of the scope tip due to passage of the needle through a curve near the tip of the scope can be monitored and compensated for via tension on actuation cables of the scope. As such, in one embodiment the memory can store instructions for (1) monitoring the tension on the cables to detect a scope tip deflection and for (2) determining tension values to apply to compensate for specific scope deflection conditions once detected. For example, once the tip of the scope is in position, the instructions can include monitoring the actuation cables for any change in tension, or for any change above a threshold level. The instructions can further identify specific cables (e.g., cable(s) located along the scope on the inside of a radius of curvature at the scope tip curve) to monitor these specific for an increase in tension, and/or can identify specific cables (e.g., cable(s) located along the scope on the outside of the radius of curvature) to monitor these specific for a decrease in tension. The instructions can also include timing parameters and/or input from a needle navigation system in order to monitor and compensate for such tension changes during a specific timeframe, for example from a time when the distal end of the needle approaches the scope tip through a time during deployment of the needle from the scope. The timing parameters can further specify that the robotic surgical system 600 should not adjust the scope tip curvature to compensate for tension changes during penetration of tissue by the needle 635 in order to maintain a straight, minimally invasive path of the needle 635 into the tissue. The scope deflection detection and compensation can, in some embodiments, be performed by an additional robotic system configured for controlling navigation of the scope in addition to or instead of the system 600 illustrated.

Although not illustrated, the robotic surgical system 600 can include other components, for example one or more input devices for receiving user input to control motion of surgical instruments (e.g., joysticks, handles, computer mice, trackpads, and gesture detection systems), instrument drivers to effect the motion of the disclosed needles, a display screen, and the like. Though described in the context of a superelastic needle, in other examples the robotic surgical system 600 can be used to control other superelastic medical tools, and can be used and in any type of medical procedures as described herein.

Overview of Example Methods of Use

Figure 7:
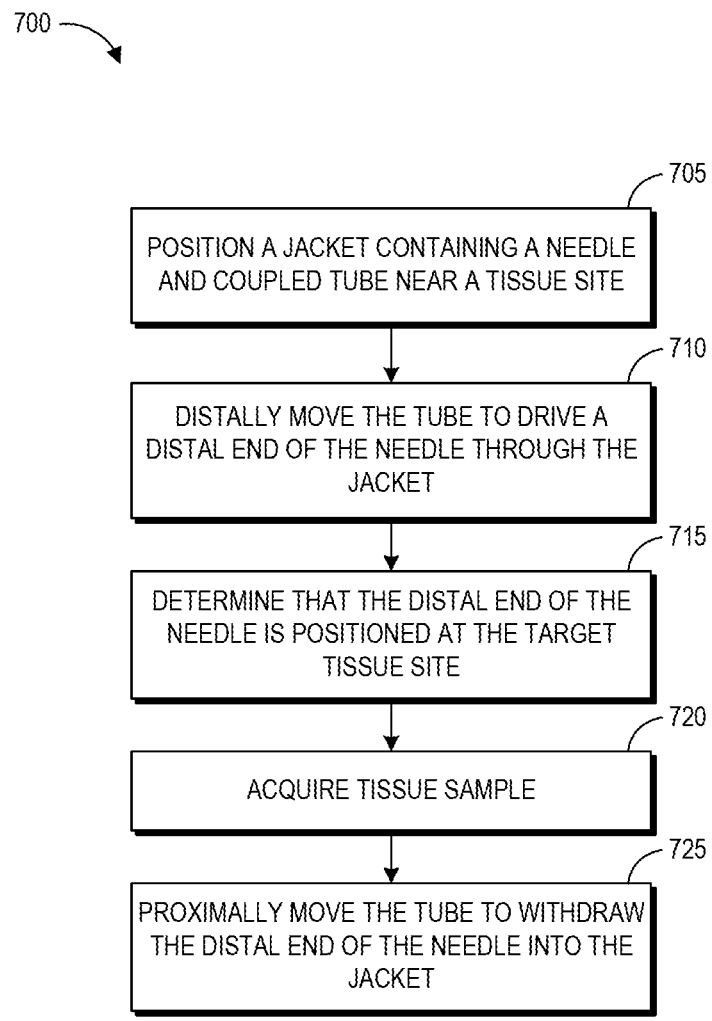
FIG. 7 depicts a flowchart of an embodiment of a process for obtaining a tissue sample using a needle as described herein.

FIG. 7 depicts a flowchart of an embodiment of a process 700 for obtaining a tissue sample using a needle as described herein, for example, needles 120, 220, 420, 556, 635 described above. The process 700 can be implemented by a human operator manually manipulating the tube secured to the needle, for example by a handle 505 as shown in FIG. 5, a robotic control system operator (such as system 600 described above) mechanically manipulating the tube as directed by a human operator or autonomously, or a combination thereof. Although described in the example context of controlling a needle to obtain a tissue sample in bronchoscopy, it will be appreciated that variations of the process 700 can be implemented using other superelastic medical tools and in other types of medical procedures as described herein.

At block 705, the operator (e.g., a human operator or autonomous surgical robot) can position a jacket 225, 550, 630 containing a needle 120, 220, 420, 556, 635 near a tissue site of a patient e.g., positioned within the reach of a needle or other medical instrument within the jacket. As described above, the needle can be positioned with its distal tip 125, 240, 559 at or near the distal end 235 of the jacket and elongate shaft 110, 210, 554, 640 can extend from the proximal end of the needle through the jacket. The jacket can be inserted through the working channel of an endoscope such as a bronchoscope in some embodiments. The elongate shaft can be coupled to a handle 505 in some embodiments for driving linear motion of the shaft relative to the jacket.

As described above, in some implementations system 600 may automatically position the endoscope 315 such that, when the needle 220 is extended from the jacket 225 into a pre-identified target tissue site, a proximal portion of the needle, a distal portion of the shaft 210, and a distal portion of the jacket 225 will remain in an overlapping position 305 within the working channel 320 of the endoscope. In some implementations, the system 600 may additionally or alternatively provide guidance for a user of the system 600 regarding maintaining such overlapping positioning. For example, the system 600 can determine that the jacket 225 is positioned within the working channel 320 of the endoscope 315 and can further determine, during or after a drive of the needle 220, that the overlap region 215 between the needle 220 and the shaft 210 is still positioned at least partly within the jacket 225. In another implementation, the system 600 can determine, during or after a drive of the needle 220, that that the overlap region 215 is still positioned at least partly within the working channel 320 of the endoscope 315. Such determinations may be made based on feedback from system 600 in some examples, for example based on robotic position data indicating the distance the needle assembly 200 is feed through the scope 210.

At block 710, the operator can distally move the shaft 210 coupled to the needle 220 to drive the distal end of the needle 220 to advance through the jacket 225. As described above and shown in the example of FIG. 5, this can involve actuation of a rotational modality of the handle, for example by rotational grip 522. Actuation of such a modality can allow the operator to exert fine control over extending the distal tip of the needle out from the distal end of the jacket. In some procedures, this can involve extending the distal tip of the needle until it has pierced patient tissue. In other implementations the tube can be advanced by instrument drivers of a robotic surgical system 600 with or without the use of such a handle. As described above, block 710 can be performed to maintain overlap between a proximal portion of the needle, a distal portion of the tube, and a distal portion of the jacket within the working channel of the endoscope. Such overlap can increase the accuracy of needle deployment by keeping the needle centered relative to the working channel.

Some implementations may initially perform blocks 705 and/or 710 in a "fast mode" that quickly takes the needle 220 to a predetermined distance from the distal end 325 of the scope 315, and thereafter a human operator may manually control (via a handle 505 or actuation via system 600) further extension of the needle 220. Some implementations may operate in a completely autonomous mode, for example by tracking the position of the needle 220 using a position sensor (e.g., an electromagnetic (EM) sensor on the needle and/or scope disposed within an EM field generated around the tissue site) so that the system 600 can determine the relative position of the needle 220, scope 315, and the tissue site.

At block 715, the operator can determine that the distal end of the needle is positioned at the target tissue site. In some implementations, a physician may view an image or video of the tissue site via an imaging device at the distal end of an endoscope working channel and may visually confirm that the needle is positioned at or within the target tissue site. For example, this can be accomplished via fluoroscopy and the physician may view the location of the radiopaque material 123, 230, 558 to discern the needle position. In some implementations, the physician may view a rendering or model of the positioning of the instrument relative to the patient tissue site to make this determination, for example as output from a robotic bronchoscopy navigation system. In some embodiments block 715 can be performed programmatically via automated image analysis and/or navigation.

At block 720, the operator can acquire a tissue sample using the needle. As described above and shown in the example of FIG. 5, this can involve a dithering motion actuated by a plunging modality, for example by plunging grip 522. Further, this can involve coupling a source of negative pressure to the proximal end of the tube, for example via fluid fitting 535.

At block 725, the operator can proximally move the tube to withdraw the distal end of the needle back into the jacket, for example via the rotational motion interface, and the jacket can be withdrawn from the patient tissue site. Any obtained sample can be expelled from the instrument for the desired analysis.

Implementing Systems and Terminology

Implementations disclosed herein provide superelastic needle assemblies and methods of using the same.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A biopsy needle assembly, comprising:
   a needle formed from a superelastic alloy, the needle including:
     a body portion extending from a distal end of the needle to a proximal end of the needle, and
     an inner surface of the needle forming a lumen extending through at least a portion of the body portion to an opening in the distal end, wherein the lumen and the opening are configured to acquire a tissue biopsy;
   an elongate member attached at the proximal end of the needle; and
   a tubular jacket including an interior channel, wherein:
     in a first configuration, the distal end of the needle is positioned within the interior channel, and
     in a second configuration, in response to distal movement of the elongate member through the interior channel, the distal end of the needle is extended beyond a distal end of the tubular jacket;
   wherein the elongate member comprises a polymer tube reflowed around an overlap region located at the proximal end of the needle; and
   wherein the needle further comprises a plurality of surface features formed on the needle at the overlap region, wherein the polymer tube is reflowed around the surface features.

2. The assembly of claim 1, wherein the superelastic alloy comprises Nitinol.

3. The assembly of claim 1, wherein the needle has a wall thickness of approximately 0.0015 inches thick.

4. The assembly of claim 1, further comprising:
   a sharpened tip at the distal end of the needle; and
   a radiopaque material positioned around the needle near the sharpened tip.

5. The assembly of claim 4, wherein the radiopaque material has a thickness of at least 200 microinches.

6. The assembly of claim 1, wherein the polymer tube comprises a conical section at the polymer tube's distal end prior to or after being reflowed around the overlap region.

7. The assembly of claim 1, wherein the needle has a length of approximately 5 centimeters from the distal end to the proximal end, and wherein the overlap region has a length of approximately 2 centimeters.

8. The assembly of claim 1, wherein the needle has a length of approximately 4 centimeters from the distal end to the proximal end, and wherein the overlap region has a length of approximately 1 centimeters.

9. The assembly of claim 1, wherein the needle has a length between 1 centimeter and 6 centimeters.

10. The assembly of claim 1, wherein the overlap region has a length of 0.5 cm to 3 cm.

11. The assembly of claim 1, wherein a channel formed by an interior surface of the polymer tube is in fluid communication with the lumen to provide pressure through the opening.

12. The assembly of claim 1, wherein the plurality of surface features comprise a grit blasted exterior surface of the needle.

13. The assembly of claim 1, wherein the plurality of surface features comprise laser cut holes each extending through a wall of the needle.

14. The assembly of claim 1, wherein the overlap region is located at a distal end of the tube, and wherein the proximal end of the needle includes a first spiral channel or cut, and the distal end of the tube includes a second spiral channel or cut structured to mechanically mate with the first spiral channel or cut.

15. The assembly of claim 1, wherein the overlap region is located at a distal end of the tube, and wherein the proximal end of the needle and the distal end of the tube are secured at the overlap region by a flexible adhesive.

16. The assembly of claim 1 wherein the overlap region is located at a distal end of the tube, and wherein the proximal end of the needle and the distal end of the tube are secured at the overlap region by screws.

17. The assembly of claim 1, wherein the superelastic alloy, in a martensite phase, deforms reversibly up to 10% from the original shape.

18. The assembly of claim 12, wherein the superelastic alloy comprises Nitinol.

19. The assembly of claim 12, wherein the needle has a wall thickness of approximately 0.0015 inches thick.

20. The assembly of claim 12, further comprising:
   a sharpened tip at the distal end of the needle; and
   a radiopaque material positioned around the needle near the sharpened tip.

21. The assembly of claim 20, wherein the radiopaque material has a thickness of at least 200 microinches.

22. The assembly of claim 12, wherein the polymer tube comprises a conical section at the polymer tube's distal end prior to or after being reflowed around the overlap region.

23. The assembly of claim 12, wherein the needle has a length of approximately 5 centimeters from the distal end to the proximal end, and wherein the overlap region has a length of approximately 2 centimeters.

24. The assembly of claim 13, wherein the superelastic alloy comprises Nitinol.

25. The assembly of claim 13, wherein the needle has a wall thickness of approximately 0.0015 inches thick.

26. The assembly of claim 13, further comprising:
   a sharpened tip at the distal end of the needle; and
   a radiopaque material positioned around the needle near the sharpened tip.

27. The assembly of claim 26, wherein the radiopaque material has a thickness of at least 200 microinches.

28. The assembly of claim 13, wherein the polymer tube comprises a conical section at the polymer tube's distal end prior to or after being reflowed around the overlap region.

29. The assembly of claim 13, wherein the needle has a length of approximately 5 centimeters from the distal end to the proximal end, and wherein the overlap region has a length of approximately 2 centimeters.

* * * * *